United States Patent
Caritu et al.

(10) Patent No.: US 8,055,021 B2
(45) Date of Patent: Nov. 8, 2011

(54) MOTION CAPTURE DEVICE AND ASSOCIATED METHOD

(75) Inventors: Yanis Caritu, St Joseph de Riviere (FR); Dominique David, Claix (FR); Christelle Godin, Brignoud (FR)

(73) Assignee: Commissariat a l'Energie Atomique, Paris (FR)

( * ) Notice: Subject to any disclaimer, the term of this patent is extended or adjusted under 35 U.S.C. 154(b) by 679 days.

(21) Appl. No.: 12/279,619

(22) PCT Filed: Feb. 16, 2007

(86) PCT No.: PCT/EP2007/051522
§ 371 (c)(1),
(2), (4) Date: Aug. 15, 2008

(87) PCT Pub. No.: WO2007/093641
PCT Pub. Date: Aug. 23, 2007

(65) Prior Publication Data
US 2009/0067678 A1    Mar. 12, 2009

(30) Foreign Application Priority Data
Feb. 17, 2006    (FR) ...................................... 06 01410

(51) Int. Cl.
*G06K 9/00*    (2006.01)
(52) U.S. Cl. ........ 382/103; 382/128; 382/107; 702/145; 702/150
(58) Field of Classification Search ................... 382/103, 382/107, 128–132; 702/145, 150–153
See application file for complete search history.

(56) References Cited

U.S. PATENT DOCUMENTS

| | | | | |
|---|---|---|---|---|
| 5,365,603 A | * | 11/1994 | Karmann | 382/291 |
| 5,719,947 A | * | 2/1998 | Enomoto et al. | 382/107 |
| 5,764,786 A | * | 6/1998 | Kuwashima et al. | 382/107 |
| 6,162,191 A | | 12/2000 | Foxlin | |
| 6,569,098 B2 | * | 5/2003 | Kawchuk | 600/437 |
| 6,820,025 B2 | | 11/2004 | Bachmann et al. | |

(Continued)

FOREIGN PATENT DOCUMENTS
EP    1593931 A1    11/2005
(Continued)

OTHER PUBLICATIONS

Marnis et al., IEEE 2001, "An Extended kalman Filter for Quaternion-Based Orientation Estimation Using MARG Sensors". (pp. 2003-2011).*

(Continued)

*Primary Examiner* — Manav Seth
(74) *Attorney, Agent, or Firm* — Pearne & Gordon LLP

(57) ABSTRACT

The invention concerns a device for capturing the motion of a structure consisting of N articulated segments, characterized in that it comprises:
first means (ML) that deliver at least one item of information able to restore an absolute acceleration vector $\vec{a}_1$ of a point on the segment of rank 1 in a reference frame forming a reference, at successive times $t_k$, k being an integer number greater than or equal to 1, and
second measuring means ($MD_1$, $MD_n$) distributed over the various segments and which deliver, for each segment of rank 1 to N, at each time $t_k$, a measurement ($M_1$, $M_n$) representing an orientation vector ($\vec{\Theta}_1$, $\vec{\Theta}_n$) of the segment in the reference frame.
Application to biomechanical analysis, telemanipulation, animation of characters, etc.

21 Claims, 9 Drawing Sheets

U.S. PATENT DOCUMENTS

| | | | |
|---|---|---|---|
| 7,263,207 B2 * | 8/2007 | Lee et al. | 382/103 |
| 7,271,827 B2 * | 9/2007 | Nister | 348/169 |
| 7,292,151 B2 * | 11/2007 | Ferguson et al. | 340/573.1 |
| 7,559,931 B2 * | 7/2009 | Stone | 606/91 |
| 7,711,516 B2 * | 5/2010 | Caritu et al. | 702/153 |
| 2003/0215130 A1 | 11/2003 | Nakamura et al. | |
| 2005/0083333 A1 | 4/2005 | Gordon | |
| 2007/0019846 A1 * | 1/2007 | Bullitt et al. | 382/128 |
| 2008/0095417 A1 * | 4/2008 | Pedrizzetti et al. | 382/128 |

FOREIGN PATENT DOCUMENTS

| | | |
|---|---|---|
| FR | 2838185 A1 | 10/2003 |
| FR | 2860700 A1 | 4/2005 |
| WO | 2005016143 A1 | 2/2005 |

OTHER PUBLICATIONS

International Search Report.

Christian Theobalt et al "Marker-free Kinematic Skeleton Estimation from Sequences of Volume Data" MPI Informatik.

L Herda et al "Skeleton-Based Motion Capture for Robust Reconstruction of Human Motion" Computer Graphics Lab (LIG) EPFL; Jan. 31, 2000; Switzerland.

International Search Report, Dated Aug. 29, 2007.

Christian Theobalt et al "Marker-free Kinematic Skeleton Estimation from Sequences of Volume Data" MPI Informatik, Nov. 2004.

* cited by examiner

| $a_1(t_k)$ | $M_1(t_k)$ | $\theta_1(t_k-1)$ | $\theta_1(t_k-2)$ | $\Rightarrow$ | $\theta_1(t_k)$ |
|---|---|---|---|---|---|
| $a_1(t_k)$ | $\theta_1(t_k)$ | $\theta_1(t_k-1)$ | $\theta_1(t_k-2)$ | $\Rightarrow$ | $a_2(t_k)$ |
| $a_2(t_k)$ | $M_2(t_k)$ | $\theta_2(t_k-1)$ | $\theta_2(t_k-2)$ | $\Rightarrow$ | $\theta_2(t_k)$ |
| $a_2(t_k)$ | $\theta_2(t_k)$ | $\theta_2(t_k-1)$ | $\theta_2(t_k-2)$ | $\Rightarrow$ | $a_2(t_k)$ |

FIG. 6B

MOTION CAPTURE DEVICE AND ASSOCIATED METHOD

TECHNICAL FIELD AND PRIOR ART

The invention concerns a motion capture device and the associated motion capture method. The invention also concerns a motion reproduction device and the associated motion reproduction method.

A device for capturing the motion of a structure is a device that measures quantities able to describe, by processing, the motion of the structure. The structure may for example be a person or robot, moving about or not.

The capture of human motion is a technique very much used in many applications: biomechanical analysis, telemanipulation, animation of a character, ergonomics, etc.

A first category of motion capture devices consists of devices that comprise two distinct parts: a first part is placed on the moving object and a second part is fixed with respect to the movement of the object. In this first category, there are mainly optical systems, electromagnetic systems and ultrasound systems. These devices are effective in terms of precision. They do however have a certain number of drawbacks. It is thus necessary to install equipment both on the object and in the environment of the object. In all cases, these systems have a short range (in keeping with the range of the physical source) and a fairly lengthy installation and calibration phase. Their cost is also very high.

The technology probably most used at the present time is based on optics, as described for example in the patent applications US 2003/0215130 A1 and US 2005/00883333 A1. These systems make it possible to reconstruct the movements of the body from images seen by cameras placed all around the scene where the action is taking place. Markers highly visible to the cameras are disposed on the moving object. Processing provides the 3D position (3D standing for "three dimensional") of each marker through the principle of stereoscopy. Despite this, the problems of optical occlusion are numerous, which makes the minimum number of cameras used high. Some authors propose reducing this type of disadvantage, as appears for example in the document entitled "Skeleton-Based Motion Capture for Robust Reconstruction of Human Motion" (L. Herda; P. Fua; R. Plänkers; R. Boulic; D. Thalmann, Computer Graph Lab (LIG), EPFL—web 01/2000). Other authors propose processing methods based on the silhouette extracted from a single camera by associating with it the model of the moving object (cf "Marker-free Kinematic Skeleton Estimation from Sequences of Volume Data" C. Theobalt; E. Aguiar; M. Magnor; H. Theisel; H-P. Seidel; MPI Informatik).

The systems based on electromagnetism reconstruct the angles and positions of the sensors disposed on the object.

Ultrasound systems, just like optical systems, find the positions of the transmitters. These two technologies suffer from the same limitation in space as camera-based technology.

A second category of device concerns devices in a single unit disposed on the moving object. This is the case with exoskeletal devices. These devices make it possible to be free of the limitation to the capture volume but are constraining since they consist of mechanical articulated arms disposed on the structure or person. The reconstruction of the movement uses measurements of angle, rather than position, between the segments of the articulated members.

More recently, systems based on a fairly old principle (the principle of inertial units) have seen the light of day on smaller scales than traditional scales, typically a few centimeters a side (cf U.S. Pat. No. 6,162,191). These devices, consisting of angular velocity sensors (gyrometers) are placed on the moving object or moving person. The angular velocity sensors supply the angles of the rotation segments provided that the measurement, which causes a drift, is integrated once. Accelerometers, or even magnetometers are sometimes associated with the gyrometers, so that, whenever the movement is slower, their measurement, based on the terrestrial magnetic and gravitational fields, reset the estimation of the orientation, thus cancelling out the drift. The capture of rapid movements does nevertheless remain a problem if the accelerations remain, since the resetting no longer occurs. In addition, gyrometers are sensors still difficult to use, fairly expensive and also having certain sensitivity to accelerations.

Another approach (cf U.S. Pat. No. 6,820,025) consists of juxtaposing with the articulated segments, angle sensors comprising gyrometers for reconstructing the movement.

The French patent application FR 2 838 185 describes a device for capturing the orientation of a solid that moves in a reference frame. The motion capture device supplies, from measurements issuing from axial or vectorial sensors placed on the solid, at least one angle of orientation $\theta$ made by the moving reference frame of the solid in the reference frame. The sensors used are preferably a magnetometer and an accelerometer. There then exists an equation (1) between the measurements M, the gravitation field G expressed in the reference frame, the magnetic field H expressed in the reference frame and the orientation angle $\theta$:

$$M = F(\theta, G, H) \tag{1}$$

The measurements M of the physical quantities that are made respectively by the accelerometer and magnetometer are thus modelled as a function F that represents the rotation $\theta$ of the reference frame attached to the solid with respect to the fixed reference frame in which the solid moves.

The orientation angle $\theta$ is derived from equation (1) by the following equation (2):

$$\theta = F^{-1}(M, G, H) \tag{2}$$

If the motion is accelerated, a new equation (3) describes the system, namely:

$$M = F(\theta, a, G, H) \tag{3}$$

The unknowns $\theta$ and a then form a space with a high dimension that, in a practical fashion, prohibits inversion of the function F. It is then not possible to extract the unknowns $\theta$ and a from equation (3). Without additional information, the device therefore does not allow the measurement of the orientation angles when the moving object is accelerated or at least when the acceleration of the moving object cannot be ignored. This represents a drawback.

The invention does not have the drawbacks of the devices mentioned above.

DISCLOSURE OF THE INVENTION

This is because the invention concerns a device for capturing the motion of a structure consisting of N successive solid segments articulated with respect to one another from a segment of rank 1 as far as a segment of rank N, N being an integer number greater than or equal to 2, the segment of rank n (n=2, ..., N) being articulated with the segment of rank n–1 at an articulation point $p_n$, characterised in that it comprises:

first means that deliver information able to restore an absolute acceleration vector $\vec{a}_1$ of a point on the segment of rank 1 in a reference frame, at successive times $t_k$, k being an integer number greater than or equal to 1, second measuring means fixed to the segment of rank 1 and which deliver, at each time $t_k$, a measurement representing an orientation vector $\vec{\Theta}_1$ of the segment of rank 1 in the reference frame, and supplementary measurement means fixed to each segment of rank n (n=2, ..., N), and which deliver, at each time $t_k$, a measurement representing an orientation vector $\vec{\Theta}_n$ of the segment of rank n.

According to a supplementary characteristic of the invention, the second measuring means and the supplementary measuring means consist of an accelerometer and a sensor that delivers a measurement of a uniform physical field present in the space where the structure moves and with a known direction in the reference frame.

According to another supplementary characteristic of the invention, the second measuring means and the supplementary measuring means comprise further at least one gyrometric axis.

According to yet another supplementary characteristic of the invention, the sensor that delivers a measurement of a uniform physical field of known direction in the reference frame is a magnetometer.

According to yet another supplementary characteristic of the invention, the sensor that delivers a measurement of a uniform physical field of known direction in the reference frame is a photoelectric cell.

According to yet another supplementary characteristic of the invention, the first means consist of a velocity measurer so that the information able to restore an absolute acceleration vector of a point on the segment of rank 1 is the velocity of the point.

According to yet another supplementary characteristic of the invention, the first means consist of a position measurer so that the information able to restore an absolute acceleration vector of a point on the segment of rank 1 is the position of the point.

The invention also concerns a device for reproducing motion of a structure consisting of N successive solid segments articulated with respect to one another from a segment of rank 1 as far as a segment of rank N, N being an integer number greater or equal to 2, the segment of rank n (n=2, ..., N) being articulated with the segment of rank n−1 at an articulation point $p_n$, characterised in that it comprises:

a motion capture device according to the invention in which the supplementary measuring means of a segment of rank n are positioned close to the articulation point $p_n$ so that the distance that separates the supplementary measuring means of a segment of rank n from the articulation point $p_n$ is considered to be zero, and calculation means that calculate, at each time $t_k$:

a) the absolute acceleration vector $\vec{a}_1$ in the reference frame, from the information delivered by the first means, b) the orientation vector $\vec{\Theta}_1$ of the segment of rank 1 in the reference frame, from the absolute acceleration vector $\vec{a}_1$ and the measurement representing the orientation vector $\vec{\Theta}_1$ of the segment of rank 1;

c) an acceleration vector $\vec{a}_n$ (n≧2) of the articulation point $p_n$ in the reference frame, from the equation:

$$\vec{a}_n = \vec{a}_{n-1} + \left(\frac{d\vec{\omega}_{n-1}}{dt}\right) \wedge \vec{L_{n-1}} + \vec{\omega}_{n-1} \wedge (\vec{\omega}_{n-1} \wedge \vec{L_{n-1}})$$

where $\vec{\omega}_n = d(\vec{\Theta}_n)/dt$ and $\vec{L}_n$ being a vector oriented from the articulation point $p_{n-1}$ to the articulation point $p_n$ and whose modulus has as its value the distance that separates the articulation point $p_n$ from the articulation point $p_{n-1}$; and d) the orientation vector $\vec{\Theta}_n$ (n≧2) of the segment of rank n from the acceleration vector $\vec{a}_n$ and the measurement representing the orientation of the segment of rank n.

The invention also concerns a device for reproducing the motion of a structure consisting of N successive solid segments articulated with respect to one another from a segment of rank 1 as far as a segment of rank N, N being an integer number greater than or equal to 2, the segment of rank n (n=2, ..., N) being articulated with the segment of rank n−1 at an articulation point $p_n$, characterised in that it comprises:

a motion capture device according to the invention in which the supplementary measuring means of a segment of rank n are distant from the articulation point $p_n$, and calculation means that calculate, at each instant $t_k$:

a) the absolute acceleration vector $\vec{a}_1$ in the reference frame, from the information delivered by the first means, b) the orientation vector $\vec{\Theta}_1$ of the segment of rank 1 in the reference frame, from the absolute acceleration vector $\vec{a}_1$ and the measurement representing the orientation vector $\vec{\Theta}_1$ of the segment of rank 1;

c) an acceleration vector $\vec{a}_n$ (n≧2) of the articulation point $p_n$ in the reference frame, from the equation:

$$\vec{a}_n = \vec{a}_{n-1} + \left(\frac{d\vec{\omega}_{n-1}}{dt}\right) \wedge \vec{L_{n-1}} + \vec{\omega}_{n-1} \wedge (\vec{\omega}_{n-1} \wedge \vec{L_{n-1}})$$

where $\vec{\omega}_n = d(\vec{\Theta}_n)/dt$, $\vec{L}_n$ being a vector oriented from the articulation point $p_{n-1}$ to the articulation point $p_n$ and whose modulus has as its value the distance that separates the articulation vector $p_n$ from the articulation point $p_{n-1}$; and d) the orientation vector $\vec{\Theta}_n$ (n≧2) and an acceleration vector $\vec{b}_n$ of the measuring point of the supplementary measuring means fixed on the segment of rank n from the acceleration vector $\vec{a}_n$, the measurement ($M_n$) representing the orientation of the segment of rank n, and the orientation vectors of the segment of rank n at least two times that precede the time $t_k$, with $\vec{b}_n$ such that:

$$\vec{b}_n = \vec{a}_n + \left(\frac{d\vec{\omega}_n}{dt}\right) \wedge \vec{D}_n + \vec{\omega}_n \wedge (\vec{\omega}_n \wedge \vec{D}_n)$$

where $\vec{D}_n$ is a vector oriented from the articulation point $p_n$ to the supplementary measuring means of the segment of rank n and whose modulus is substantially equal to the distance that separates the articulation point $p_n$ of the supplementary measuring means of the segment of rank n.

According to an additional characteristic of the invention, radio transmission means transmit elementary electrical signals representing the measurements delivered by the first measuring means and the second measuring means to the calculation means.

According to yet another additional characteristic of the invention, the radio transmission means comprise an intermediate unit that receives the elementary electrical signals and that retransmits an electrical signal representing the elementary electrical signals to the calculation means.

According to yet another additional characteristic of the invention, storage means store the measurements delivered by the first measuring means and the second measuring means.

According to yet another additional characteristic of the invention, the storage means are placed on the structure.

The invention also concerns:
- a motion capture method according to independent claim 14,
- a motion reproduction method according to independent claim 18, and
- a motion reproduction method according to independent claim 19.

An elementary measuring device according to the invention consists of two types of sensor, one of which is an accelerometer.

Preferentially, an elementary measuring device is produced by means of a device for capturing solid rotation motion as described in the French patent application published under the reference FR 2 838 185 and filed, in the name of the applicant, on 5 Apr. 2002. An elementary measuring device thus consists of a pair (accelerometer, sensor X).

Sensor X means any sensor that supplies a measurement of a uniform physical field present in the space where the moving body is moving, physical field whose direction is known in the reference frame or which is measured in a reference position. The only constraints concerning the sensor X are firstly that the sensor must not be sensitive to acceleration and secondly that the direction of the physical field measured is different from the vertical. The sensor X can thus be a magnetometer that measures the direction of the terrestrial magnetic field. The sensor X can also be a photoelectric cell whose measurement is that of the light intensity that arrives on the cell. If for example, the illumination source is the sun and the date, time, longitude and latitude are known when the light intensity is measured, the angle of incidence of the solar ray in an absolute reference frame can be predicted and consequently the measurement is modulated according to the angle that the device makes with respect to the direction of the solar ray. This is therefore also another way of measuring an angle. The sensor X can also consist of one or more gyrometric axes that supplement the measurement of the accelerometer.

The first means that deliver information able to restore an absolute acceleration vector $\vec{a}_1$ of a point on the segment of rank 1 can be implemented by a system of local measurements. A simple accelerometer is not suitable if means are not available for compensating for the acceleration of gravity. In the concrete case of the measurement of the movement of a person, the local measurement system can advantageously be placed at the centre of gravity or close to the centre of gravity of the body of the person (at the waist, for example).

The system of local measurements may for example be a device of the GPS type (GPS standing for "Global Positioning System") associated with a differentiating circuit. The GPS device makes it possible to know at any time the position of the element that carries it and a differentiating circuit, by differentiating the position data twice, determines the absolute acceleration in the geographical reference frame.

The system of local measurements can also be implemented by means of a radio location device associated with a differentiating circuit. Radio location devices require the use of beacons (ULB radar (ULB standing for "Ultra Large Band"), optical beacon, etc). Radio location devices therefore cause the autonomous character of the local measuring system to be lost. They do however prove to be very advantageous in use when following movements in an enclosure where beacons are first positioned. The use of radio systems also has the dual advantage of the data transmission and position measurement (this is particularly the case with ULB devices). Just as in the case of the GPS device, the position measurement delivered by the radio location device is differentiated twice in order to obtain the acceleration measurement.

An oriented pressure measurement (tube) is directly correlated with the velocity of a body in air. It is thus possible to determine, along three axes, the velocity vector of a segment to which a pressure measurer is fixed. By differentiating the velocity measurement once, the acceleration is obtained.

The motion capture device can advantageously be "dynamic" with regard to the hierarchical structure of the moving structure. In the case for example of a humanoid structure (person or robot), this means that the local measuring system or systems ML may be placed either at the foot, the hand, the waist, etc, or any other part of the body that can be assimilated to a rigid element.

In other embodiments of the invention, the first means that deliver information able to restore an absolute acceleration vector $\vec{a}_1$ of a point on the segment of rank 1 are not measuring means. Where it is known that a point on a segment is fixed in the reference frame, it is in fact unnecessary to make an acceleration measurement on this segment. This segment can then advantageously be chosen as the segment of rank 1. The first means that deliver the information able to restore an absolute acceleration vector $\vec{a}_1$ of a point on the segment of rank 1 may therefore for example be storage means that have knowledge of the fixed position occupied by a point on the segment of rank 1 in the reference frame.

By way of non-limitative example, in the remainder of the description, the first means that deliver information able to restore an absolute acceleration vector $\vec{a}_1$ are measuring means ML fixed to the segment of rank 1. The measuring means ML will be considered to be superimposed on the second measuring means $MD_1$, which are also fixed to the segment of rank 1. In a more general case, the measuring means ML and $MD_1$ are distant from each other, the position of the measuring means ML then being able to be assimilated to a virtual point of articulation between the segment of rank 1 and a virtual segment of rank zero.

A measuring device MD can characterise an idle state. The variance of the signals delivered by the device MD is then below a threshold. As soon as an idle state is detected at a point, there exists a very high probability for this point to be at rest in the fixed reference frame (this is because, although a uniform rectilinear movement gives the same result as an idle state, such a movement is improbable and difficult to maintain). In the case of rest detected, the acceleration of the structure is zero and the state of rest can be detected.

However, there are cases where an articulation is at rest in a particular movement. This is the case for example in walking where each foot is momentarily at rest alternately. In this case, the method of the invention applies so that the segment of rank 1 is alternately the right foot or the left foot.

In the remainder of the description, the invention will be described for the capture and reproduction of the movement of an articulated structure consisting of a succession of segments. However, it is clear that the invention also applies to any non-articulated solid body of any form (this may then be identified with the segment of rank 1 of the articulated structure described) or to a complex articulated structure consisting of several sets of articulated segments.

BRIEF DESCRIPTION OF THE DRAWINGS

Other characteristics and advantages of the invention will emerge from a reading of a preferential embodiment given with reference to the accompanying figures, among which:

FIG. 6B illustrates, in the general case, the results of calculation, gradually, of the acceleration and orientation data obtained for the various segments of a structure with articulated segments;

In all the figures, the same references represent the same elements.

DETAILED DESCRIPTION OF EMBODIMENTS OF THE INVENTION

Figure 1:
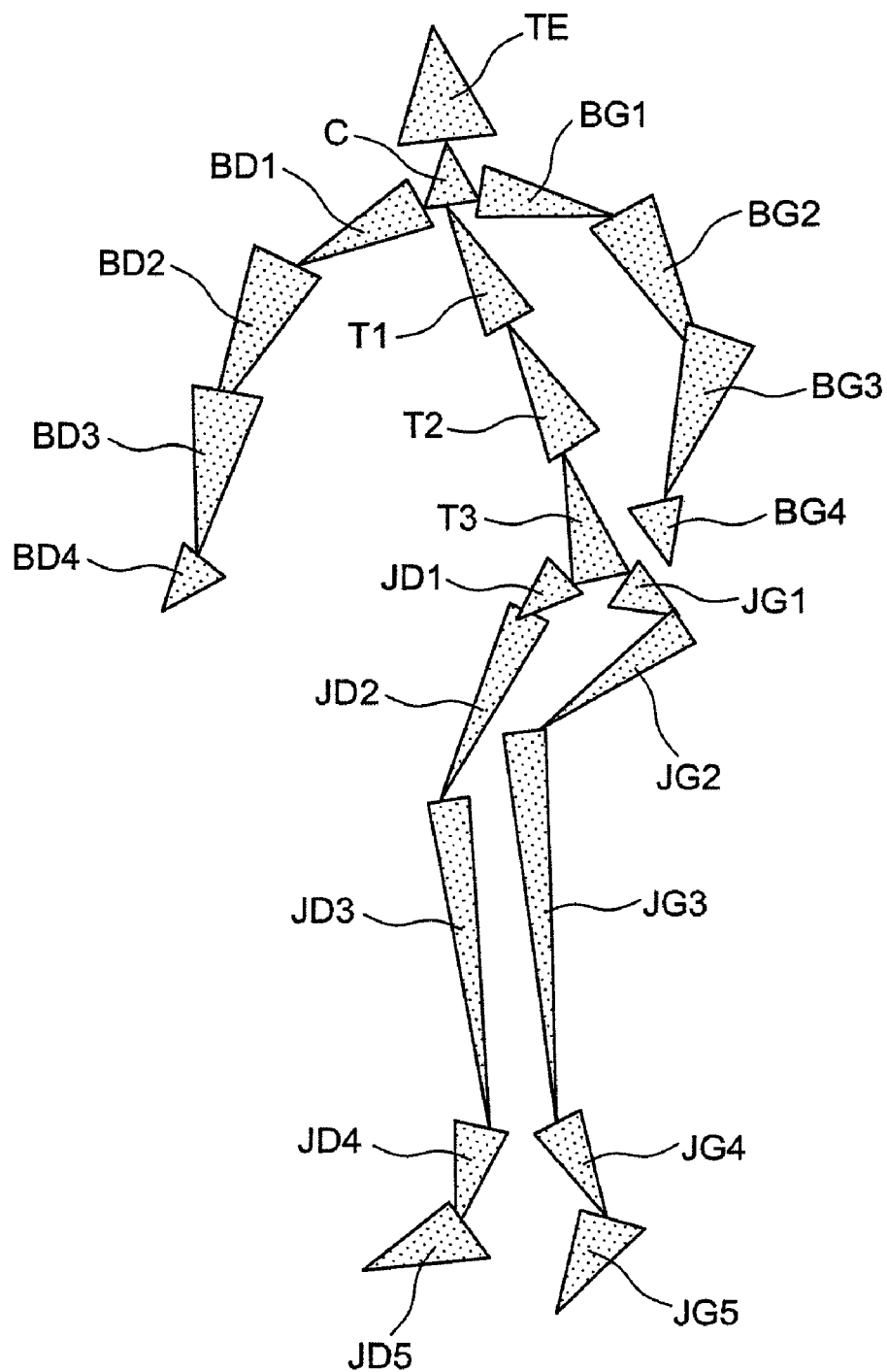
FIG. 1 depicts, symbolically, an example of an articulated structure to which the motion capture device of the invention relates.

FIG. 1 depicts an example of an articulated structure to which the motion capture device of the invention relates.

The structure, for example a human body or a humanoid robot, is broken down into a set of segments which are so many solid elements articulated with respect to one another. All the segments are thus broken down into a head segment TE, a neck segment C, a set of trunk segments T1, T2, T3, a set of left arm segments BG1, BG2, BG3, GB4, a set of right arm segments BD1, BD2, BD3, BD4, a set of left leg segments JG1, JG2, JG3, JG4, JG5 and a set of right leg segments JD1, JD2, JD3, JD4, JD5.

Figure 2:
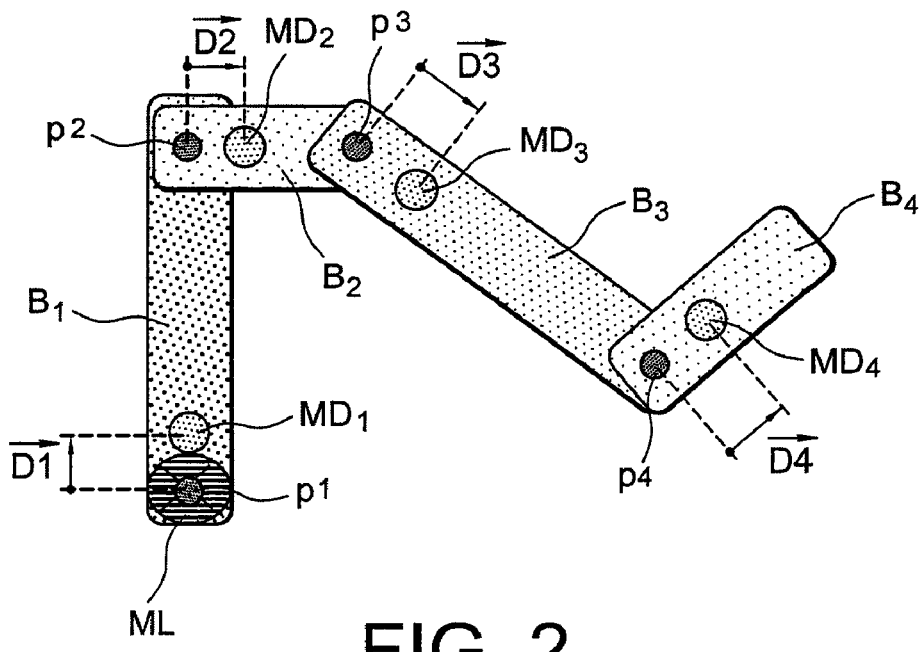
FIG. 2 depicts an example of a motion capture device according to the invention in the case of a structure with four articulated segments.

FIG. 2 depicts an articulated structure provided with a motion capture device according to the invention. The structure is for example a robot arm consisting of four articulated segments $B_1$, $B_2$, $B_3$, $B_4$ ranging from the shoulder to the hand.

The segment $B_1$ is provided with a system of local measurements ML and an elementary orientation-measurements device $MD_1$. The elementary orientation-measurements device $MD_1$ is distant from the local-measurements system ML. The fixing point of the local-measurements system ML and the fixing point of the elementary orientation-measurements device $MD_1$ define a vector $\vec{D}_1$ of modulus $D_1$ oriented from ML towards $MD_1$. As mentioned previously, when a point on the segment of rank 1 is fixed, the local-measurement system ML is unnecessary since it is then known that the acceleration of this point is zero in the reference frame.

Each segment $B_n$ (n=2, 3, 4) is provided with an articulation point $p_n$ where the adjoining segment $B_{n-1}$ is articulated. An elementary orientation-measurements device $MD_n$ is placed on each segment $B_n$. The fixing point of the elementary orientation-measurements device $MD_n$ is distant from the articulation point $p_n$, the fixing point of the elementary orientation-measurements device $MD_n$ and the articulation point $p_n$ defining a vector $\vec{D}_n$ of modulus $D_n$ and oriented from $p_n$ towards $MD_n$.

The function of the motion reproduction device of the invention is to estimate, gradually, from the knowledge of the acceleration and orientation of the first segment $B_1$, the acceleration of the successive articulation points of the various segments as well as the angles that the various segments make to each other.

In the following diagrams and discussions, n is the generic index, or rank, of a segment, k is a generic time incrementation index, $a_n$ is the acceleration of the articulation point $p_n$ of the segment of rank n in a fixed reference frame and $\theta_n$ is the orientation in three dimensions (3D orientation) of the segment of rank n in the fixed reference frame. For reasons of convenience, the accelerations $a_n$ and orientations $\theta_n$ are usual denoted in scalar form in the patent application. It must however be noted that all these quantities are third-dimension vectors in the reference frame.

Figure 3:
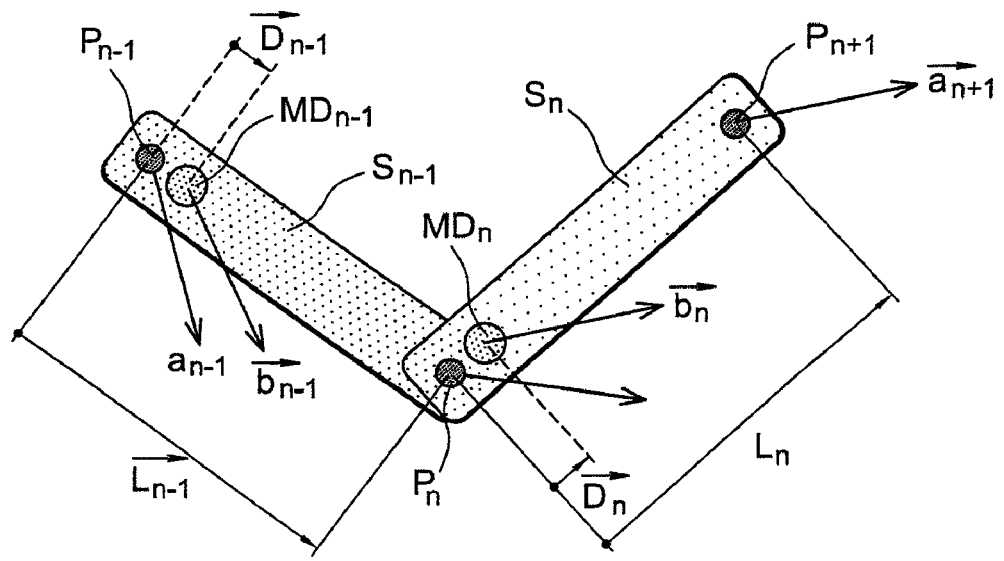
FIG. 3 depicts two successive articulated segments provided with a motion capture device according to the invention.

FIG. 3 depicts a detail view of a moving structure equipped with a motion capture device of the invention. A segment $S_n$ is articulated with a segment $S_{n-1}$ at an articulation point $p_n$. The length of the segment $S_n$ is assimilated to the distance $L_n$ that separates the articulation point $p_{n+1}$ from the articulation point $p_n$. Likewise, the length of the segment $S_{n-1}$ is assimilated to the distance $L_{n-1}$ that separates the articulation point $p_n$ from the articulation point $p_{n-1}$. The articulation points $p_{n-1}$ and $p_n$ define a vector $\vec{L}_n$ oriented from $p_{n-1}$ towards $p_n$ and whose modulus is equal to the distance that separates the articulation points $p_n$ and $p_{n-1}$. The articulation point $p_n$ has an acceleration $a_n$ and the articulation point $p_{n-1}$ has an acceleration $a_{n-1}$. The measurement points of the devices $MD_n$ and $MD_{n-1}$ on the respective segments of rank n and n−1 have the respective accelerations $b_n$ and $n_{n-1}$.

In the remainder of the description, the invention will be presented firstly in the particular case where the vectors $\vec{D}_n$ are negligible (the vectors $\vec{D}_n$ are then consider to be zero vectors) and secondly in the general case where the vectors $\vec{D}_n$ are not considered to be negligible.

Figure 4A:
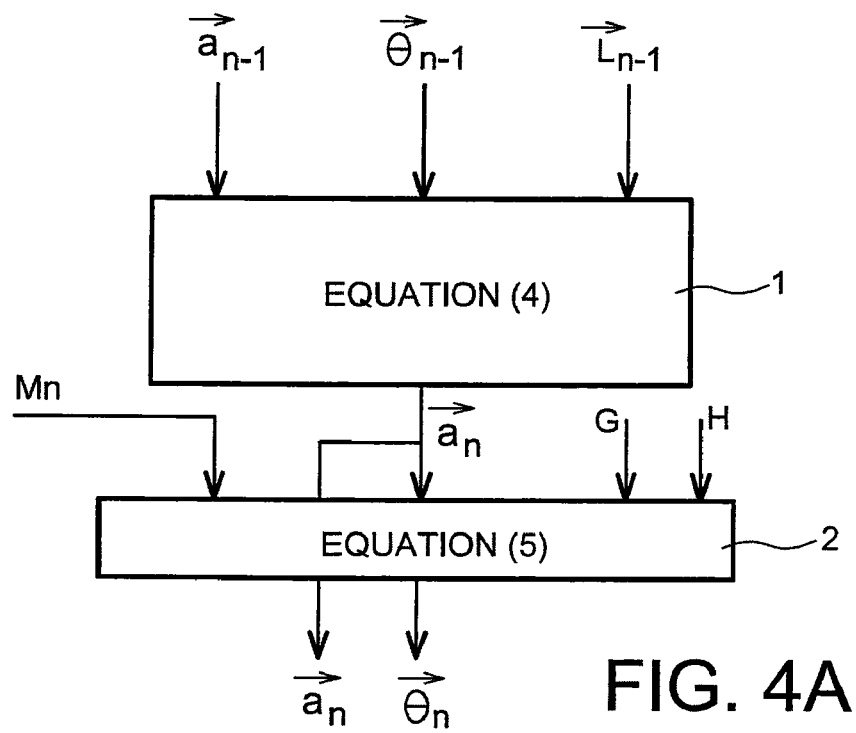
FIG. 4A depicts essential steps of a particular case of the measurement processing method used in the context of the invention.

FIG. 4A depicts the general principle of determining quantities $\vec{a}_n$ and $\vec{\Theta}_n$ according to the invention in the particular case where the vectors $\vec{D}_n$ are zero. The acceleration $\vec{a}_n$ of the articulation point $p_n$ is calculated from the acceleration $\vec{a}_{n-1}$ of the articulation point $p_{n-1}$, the vector $\vec{L}_{n-1}$ that represents the segment of rank n−1 and the vector $\vec{\Theta}_{n-1}$ that represents the 3D orientation vector of the segment of rank n−1. This gives, in accordance with the motion composition law:

$$\vec{a}_n = \vec{a}_{n-1} + \left(\frac{d\vec{\omega}_{n-1}}{dt}\right) \wedge \overrightarrow{L_{n-1}} + \vec{\omega}_{n-1} \wedge (\vec{\omega}_{n-1} \wedge \overrightarrow{L_{n-1}}) \quad (4)$$

in which:
the symbol "∧" represents the "vectorial product" operator, and
$\vec{\omega}_{n-1} = d(\vec{\Theta}_{n-1})/dt$ The acceleration $\vec{a}_n$ being a known quantity, it is then possible to calculate the orientation $\vec{\Theta}_n$ on the basis of equation (5):

$$\vec{\Theta}_n = F^{-1}(M_n, \vec{a}_n, G, H) \quad (5)$$

in which:
$M_n$ represents the measurements delivered by the elementary measurements device $MD_n$ placed on the segment of rank n, and
G and H are respectively the gravitation field and the magnetic field measured in the reference frame, at the segment of rank n.

Equation (5) is an equation known per se that corresponds to equation (2) given above.

Figure 4B:
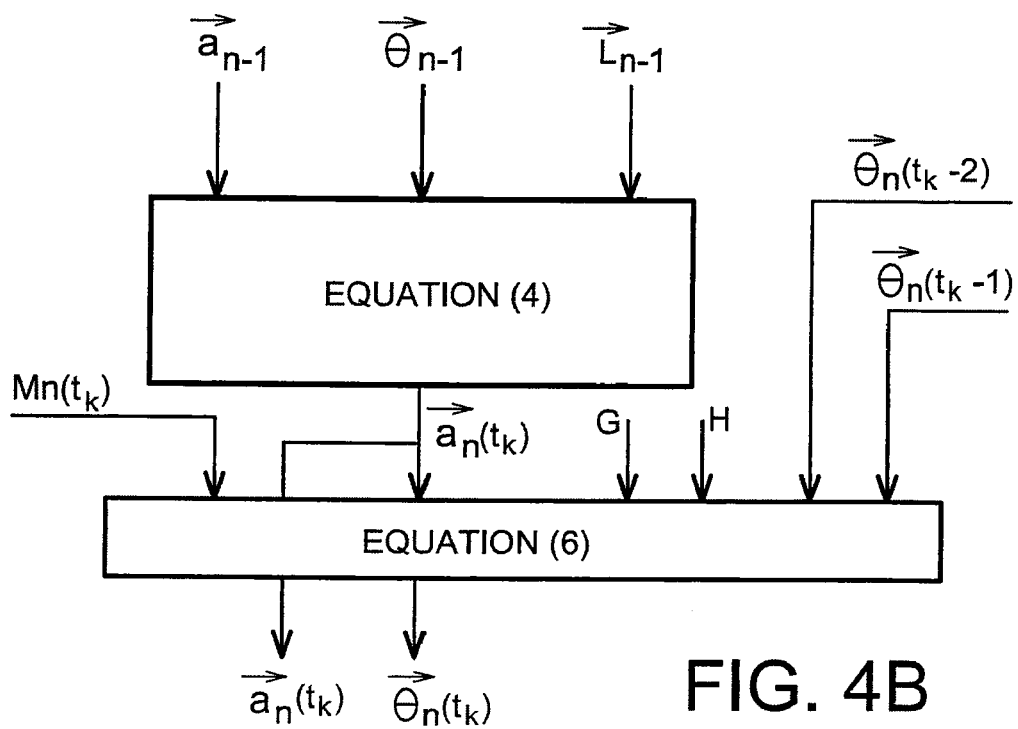
FIG. 4B depicts, in the general case, essential steps of the measurement processing method used in the context of the invention.

FIG. 4B depicts, in the general case, the essential steps of the measurement processing method used in the context of the invention. In the general case, the equation that connects the acceleration $\vec{b}_n$ of the measuring point of the device $MD_n$ and $\vec{\Theta}_n$ is written:

$$\vec{b}_n = \vec{a}_{n-1} + \left(\frac{d\vec{\omega}_{n-1}}{dt}\right) \wedge \overrightarrow{L_{n-1}} + \vec{\omega}_{n-1} \wedge (\vec{\omega}_{n-1} \wedge \overrightarrow{L_{n-1}}) + \left(\frac{d\vec{\omega}_n}{dt}\right) \wedge \vec{D}_n + \vec{\omega}_n \wedge (\vec{\omega}_n \wedge \vec{D}_n)$$

or again:

$$\vec{b}_n = \vec{a}_n + \left(\frac{d\vec{\omega}_n}{dt}\right) \wedge \vec{D}_n + \vec{\omega}_n \wedge (\vec{\omega}_n \wedge \vec{D}_n)$$

It is then possible to write the quantity $b_b(t_k)$ in the following form:

$$b_n(t_k) = K(\vec{a}_n(t_k), \vec{\Theta}_n(t_{i<k}), \vec{\Theta}_n(t_k))$$

The vector $\vec{a}_n$ is then calculated by means of equation (4) as it was before in the particular case described above. Next the vectors $\vec{b}_n$ and $\vec{\Theta}_n$ are calculated, at time $t_k$, using equation (6) such that:

$$\vec{\Theta}_n(t_k) = L^{-1}(M_n(t_k), \vec{a}(t_k), G, H, \vec{\Theta}_n(t_{i<k})) \quad (6)$$

where the function L is a function that combines the functions F and K so that:

$$M_n(t_k) = F(\vec{b}_n(t_k), G, H, \vec{\Theta}_n(t_k))$$
$$= F[K(\vec{a}_n(t_k), \vec{\Theta}_n(t_{i<k}), \vec{\Theta}_n(t_k)), G, H, \vec{\Theta}_n(t_k)]$$
$$= L(\vec{a}_n(t_k), G, H, \vec{\Theta}_n(t_k), \vec{\Theta}_n(t_{i<k}))$$

Figure 5A:
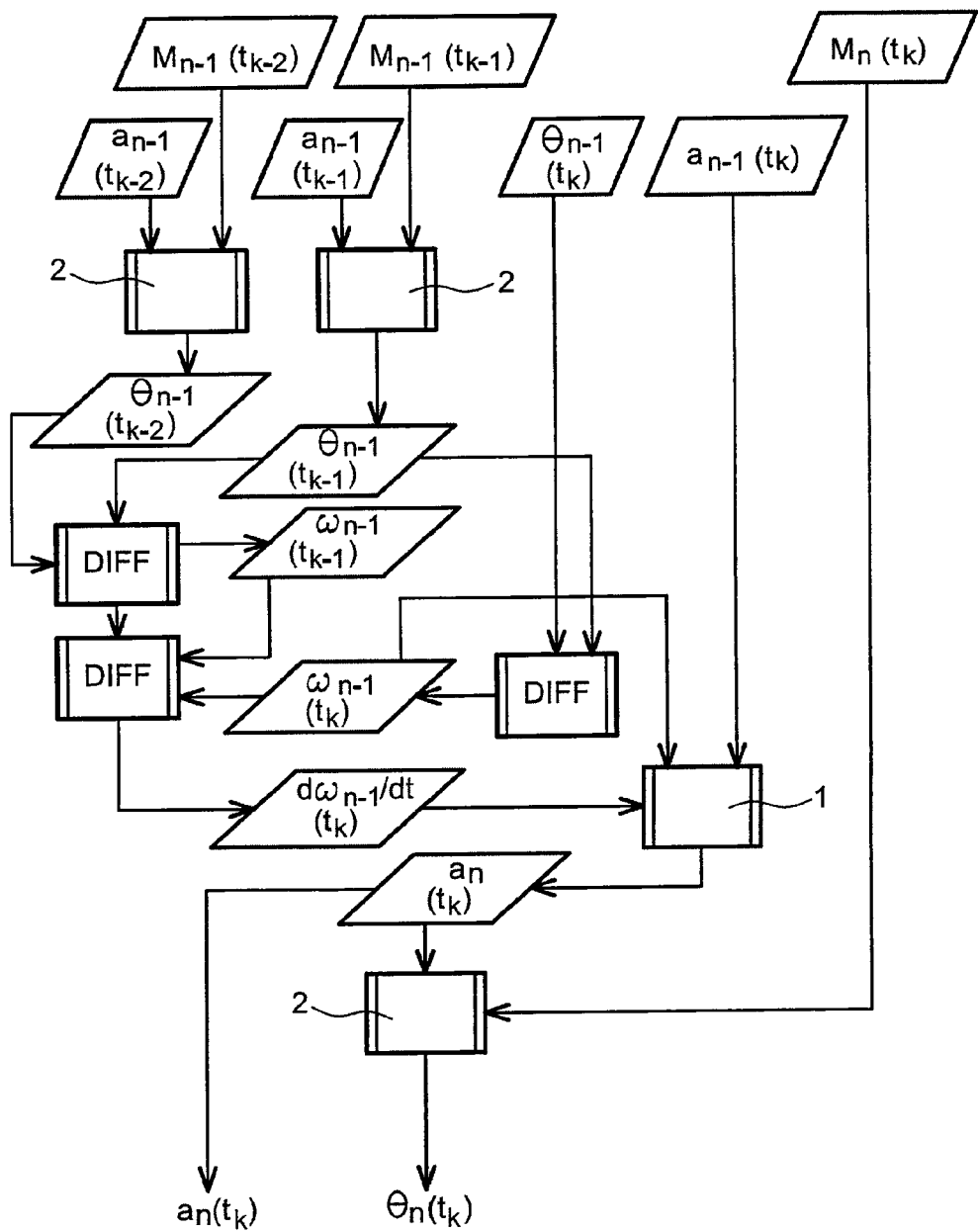
FIG. 5A depicts a detailed flow diagram of an essential step of the measurement processing method shown in FIG. 4A.

FIG. 5A depicts a detailed flow diagram of an essential step of the measurement processing method depicted in FIG. 4A.

The processing unit depicted in FIG. 5A details the calculation of the quantities $a_n(t_k)$ and $\theta_n(t_k)$, which are associated, at a time $t_k$, with the segment of rank n. The quantities $a_n(t_k)$ and $\theta_n(t_k)$ of the segment of rank n are determined from the following measured or calculated data:
the accelerations $a_{n-1}(t_k)$, $a_{n-1}(t_{k-1})$ and $a_{n-1}(t_{k-2})$ relating to the segment of rank n−1, calculated for three different times $t_k$, $t_{k-1}$, $t_{k-2}$, and
the measurements $M_{n-1}(t_{k-1})$ and $M_{n-1}(t_{k-2})$ delivered, by the elementary measurements device $MD_{n-1}$, at the two different times $t_{k-1}$ and $t_{k-2}$,
the orientation $\theta_{n-1}(t_k)$ of the segment of rank n−1 calculated at time $t_k$, and
the measurements $M_n(t_k)$ delivered by the elementary measurements device $MD_n$ at time $t_k$.

The quantities $a_{n-1}(t_{k-2})$ and $M_{n-1}(t_{k-2})$ are applied to an operator 2, which uses equation (5) and delivers the orientation $\theta_{n-1}(t_{k-2})$. Likewise the quantities $a_{n-1}(t_{k-1})$ and $M_{n-1}(t_{k-1})$ are applied to an operator 2 that uses equation (5) and delivers the orientation $\theta_{n-1}(t_{k-1})$.

The quantities $\theta_{n-1}(t_{k-2})$ and $\theta_{n-1}(t_{k-1})$ and the interval of time information $\Delta t_{21}$ such that:

$$\Delta t_{21} = t_{k-2} - t_{k-1}$$

are next applied to a differentiating operator DIFF that calculates the quantity $\omega_{n-1}(t_{k-1})$ such that:

$$\omega_{n-1}(t_{k-1}) = (\theta_{n-1}(t_{k-2}) - \theta_{n-1}(t_{k-1}))/\Delta t_{21}.$$

The quantities $\omega_{n-1}(t_k)$ and $d(\omega_{n-1}(t_k))/dt$ are then calculated:
the quantity $\omega_{n-1}(t_k)$ is calculated by means of a differentiating operator DIFF so that: $\omega_{n-1}(t_k) = (\theta_{n-1}(t_{k-1}) - \theta_{n-1}(t_k))/\Delta t_{10}$, where $\theta_{n-1}(t_{k-1})$, is the quantity calculated above, $\theta_{n-1}(t_k)$ is known (calculated previously), and $\Delta t_{10} = t_{k-1} - t_k$, and
the quantity $d(\omega_{n-1}(t_k))/dt$ is calculated by means of a differentiating operator DIFF so that: $d(\omega_{n-1}(t_k))/dt = (\omega_{n-1}(t_{k-1}) - \omega_{n-1}(t_k))/\Delta t_{10}$, where $\omega_{n-1}(t_{k-1})$ and $\omega_{n-1}(t_k)$ are the quantities calculated above, and $\Delta t_{10} = t_{k-1} - t_k$.

The quantities $a_{n-1}(t_k)$, $\omega_{n-1}(t_k)$ and $d(\omega_{n-1}(t_k))/dt$ are then applied to an operator 1, which uses equation (4) and delivers the quantity $a_n(t_k)$. The calculated quantity $a_n(t_k)$ and the known measurement taken $M_n(t_k)$ are then applied to an operator 2 that uses equation (5) and delivers the orientation quantity $\theta_n(t_k)$.

The processing of the measurements acquired by the articulated motion capture device of the invention leads to the determination, for each segment of the moving structure, of its acceleration at the articulation point and its orientation in a reference frame. It is then possible to describe the motion of the structure, for example on a screen.

As appears clearly with reference to FIG. 5A, the determination of the pair $[a_n(t_k), \theta_n(t_k)]$ of a segment of rank n at time $t_k$ is deduced, amongst other things, from information relating to the segment of rank n−1 at the prior times $t_{k-1}$ and $t_{k-2}$. Consequently it is clear that not all the acceleration and orientation data relating to all the segments of the structure can be known as from the first measurement. It is thus necessary to acquire a certain number of measurements before the articulated motion can be reproduced in its entirety.

Figure 5B:
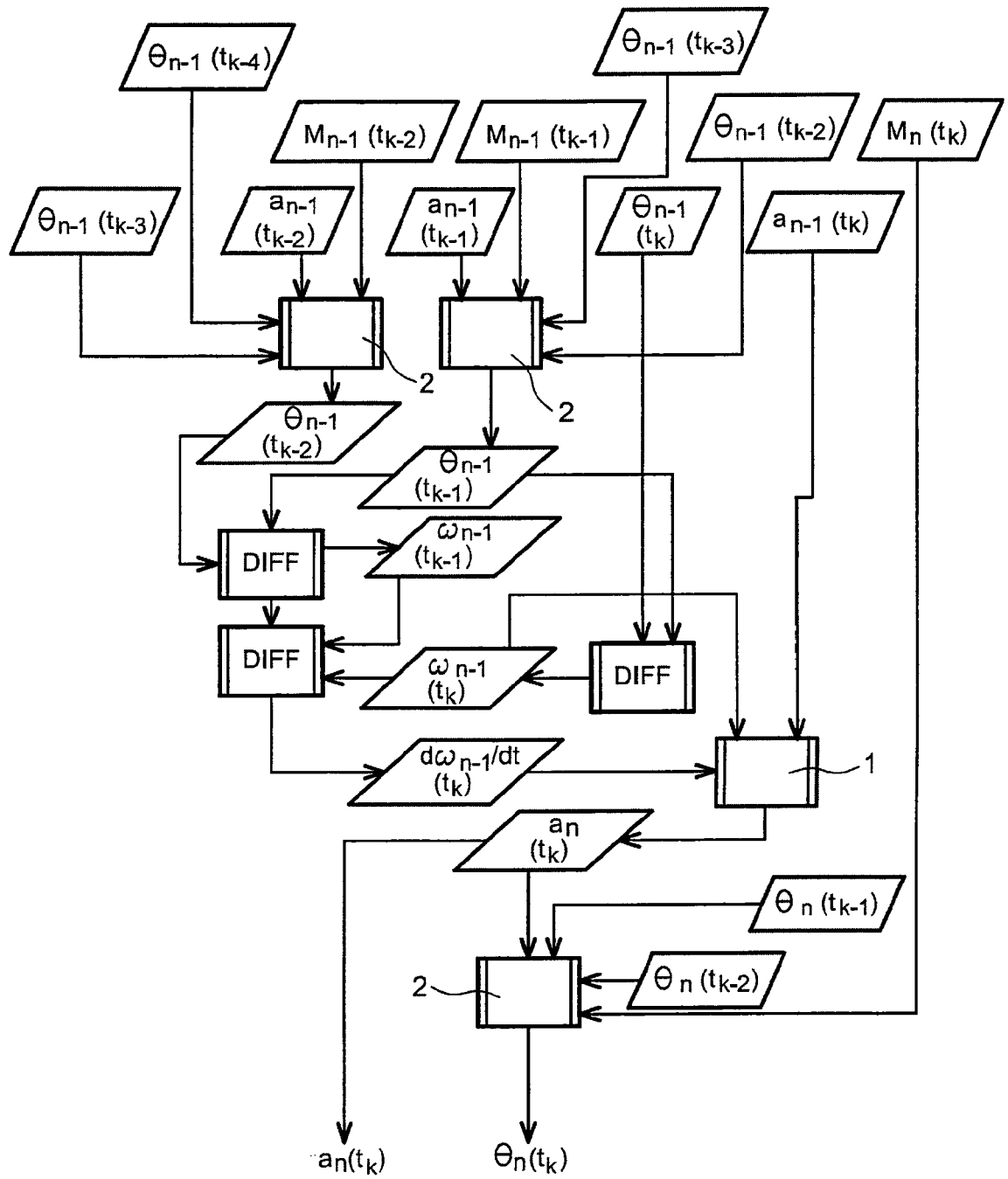
FIG. 5B depicts a detailed flow diagram of an essential step of the measurement processing method shown in FIG. 4B.

FIG. 5B depicts a detailed flow diagram of an essential step of the measurement processing method depicted in FIG. 4B.

In addition to the data mentioned with reference to FIG. 5A, the quantities $\vec{a}_n(t_k)$ and $\vec{\Theta}_n(t_k)$ relating to the segment of rank n are here also determined from the orientations $\theta_n(t_{k-1})$ and $\theta_n(t_{k-2})$ calculated, for the segment n, at times $t_{k-1}$ and $t_{k-2}$.

The quantities $a_{n-1}(t_{k-2})$, $\theta_{n-1}(t_{k-3})$, $\theta_{n-1}(t_{k-4})$ and $M_{n-1}(t_{k-2})$ are then applied to an operator 2 that used equation (6) and delivers the orientation $\theta_{n-1}(t_{k-2})$. Likewise, the quantities $a_{n-1}(t_{k-1})$, $\theta_{n-1}(t_{k-2})$, $\theta_{n-1}(t_{k-3})$ and $M_{n-1}(t_{k-1})$ are applied to an operator 2, which uses equation (6) and delivers the orientation $\theta_{n-1}(t_{k-1})$.

The quantities $a_{n-1}(t_k)$, $\omega_{n-1}(t_k)$ and $d(\omega_{n-1}(t_k))/dt$ are then applied to an operator 1, which uses equation (4) and delivers the quantity $a_n(t_k)$. The orientations $\theta_n(t_{k-1})$ and $\theta_n(t_{k-2})$ estimated at the two times preceding time $t_k$, the calculated quantity $a_n(t_k)$ and the known measurement sample $M_n(t_k)$ are then applied to an operator 2, which uses equation (6), where $\omega_n(t_k)$ and $d\omega(t_k)$ are given as before by the operator DIFF:

$$\omega_n(t_k) = (\theta_n(t_{k-1}) - \theta_n(t_k))/\Delta t \quad 10$$

$$d(W_n(t_k))/dt = (W_n(t_{k-1}) - W(t_k))/\Delta t \quad 10$$

where $$W_n(t_{k-1}) = (\theta_n(t_{k-2}) - \theta_n(t_{k-1}))/\Delta t \quad 21$$

The operator 2 then delivers the orientation quantity $\theta_n(t_k)$.

The processing of the measurements acquired by the articulation motion capture device of the invention leads to the determination, for each segment of the moving structure, of its acceleration at the articulation point and its orientation in a reference frame. It is then possible to describe the movement of the structure, for example on a screen.

As appears clearly, for example with reference to FIG. 5A, the determination of the pair $[a_n(t_k), \theta_n(t_k)]$ of a segment of rank n at time $t_k$ is deduced, amongst other things, from information relating to the segment of rand n−1 at the prior times $t_{k-1}$ and $t_{k-2}$. Consequently it is clear that not all the acceleration and orientation data relating to all the segments of the structure can be known as from the first measurement. It is thus necessary to acquire a certain number of measurements before the articulated movement can be reproduced in its entirety.

Likewise, in the general case where the vectors $\vec{D}_n$ are not considered to be zero, it is necessary to know two previous successive orientations of the segment of rank n in order to initialise the method. These orientations can be obtained for example when the segment is immobile using the method described in the patent application FR 2 838 185. On the other hand, as shown above, where the measuring means representing the orientation of the segment of rank n are sufficiently close to the articulation point $p_n$, it is not necessary to know the two previous successive orientations and the method is simplified.

Figure 6A:
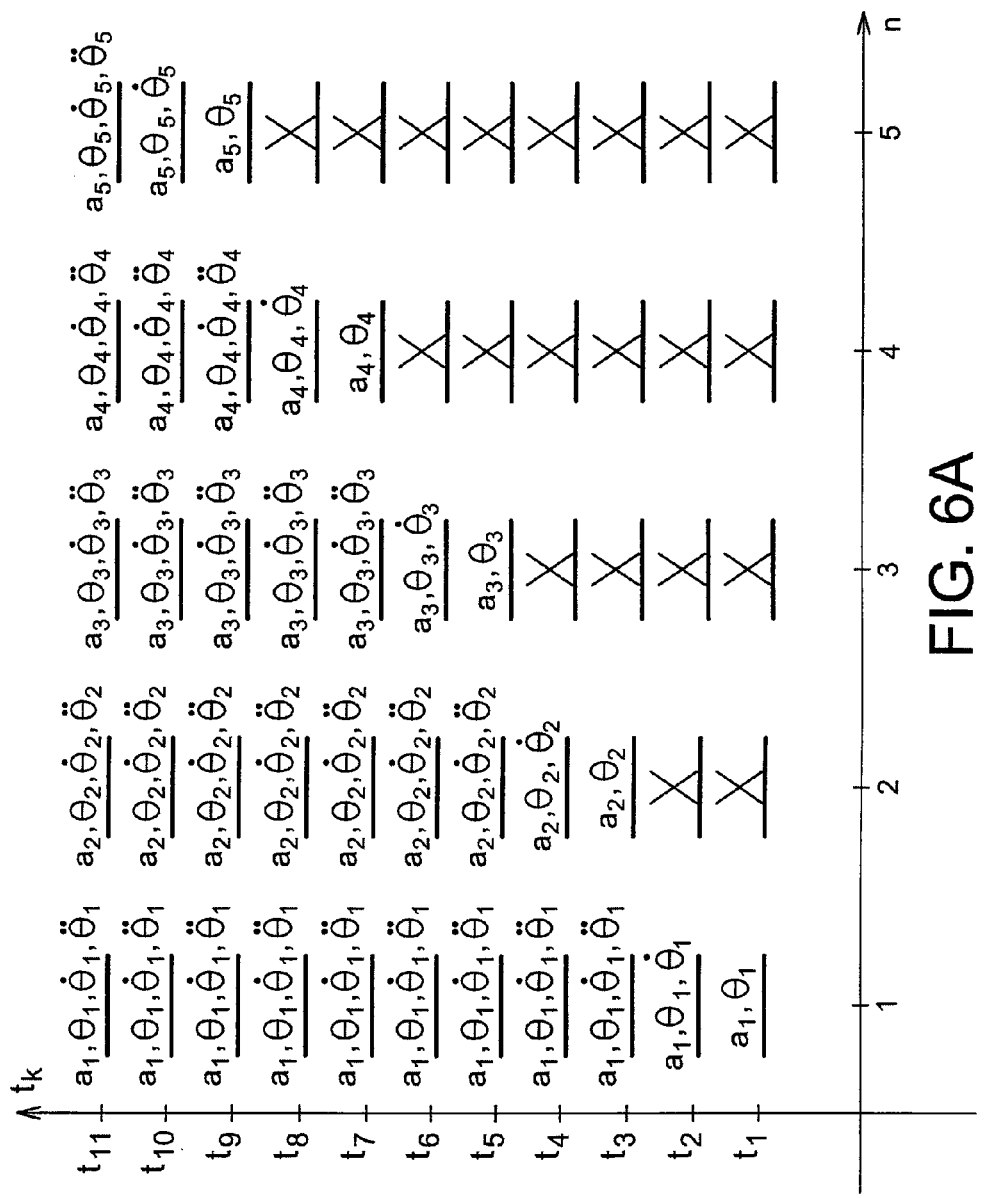
FIG. 6A illustrates, symbolically, in the particular case mentioned above, the change over time of the acceleration and orientation data obtained for the various segments of a structure with five articulated segments.

FIG. 6A illustrates, symbolically, in the particular case where the vectors $\vec{D}_n$ are considered to be zero, the change over time of the acceleration and orientation data obtained for the various segments of a structure with five articulated segments.

In FIG. 6A, the horizontal axis represents the rank n of the segments that make up the structure and the vertical axis represents the successive measurement times $t_k$. At the intersection of a rank n and a time $t_k$ there are indicated the quantities (acceleration and orientation) that are known at time $t_k$, for the segment of rank n. These quantities consist of measurement data and/or data deduced from measurement data.

In order not to burden FIG. 6A, the quantity $d\theta_n/dt$ is represented by the symbol $\dot{\theta}_n$ and the quantity $d^2\theta_n/dt^2$ is represented by the symbol $\ddot{\theta}_n$. Moreover, this gives:

$d\theta_n(t_k) = \theta_n(t_k) - \theta_n(t_{k-1})$, $dt(t_k) = t_k - t_{k-1}$, $d^2\theta_n(t_k) = d\theta_n(t_k) - d\theta_n(t_{k-1})$, $dt^2(t_k) = t_k - t_{k-1}$.

At time $t_1$, the only known quantities relating to the segments are as follows:

$a_1(t_1)$, $\theta_1(t_1)$

These data are of course insufficient to describe the motion of the structure.

At time $t_2$, the known quantities relating to the segments of ranks 1 to 5 are as follows:

$a_1(t_2)$, $\theta_1(t_2)$, $d\theta_1/dt(t_2)$

These data are still insufficient to describe the motion of the structure.

At time $t_3$, the known quantities relating to the segments are as follows:

$a_1(t_3)$, $\theta_1(t_3)$, $d\theta_1/dt(t_3)$, $d^2\theta_1/dt^2(t_3)$, $a_2(t_3)$, $\theta_2(t_3)$.

These data are still insufficient to describe the motion of the structure.

At time $t_4$, the known quantities are as follows:

$a_1(t_4)$, $\theta_1(t_4)$, $d\theta_1/dt(t_4)$, $d^2\theta_1/dt^2(t_4)$, $a_2(t_4)$, $\theta_2(t_4)$, $d\theta_2/dt(t_4)$.

These data are still insufficient to describe the motion of the structure.

At time $t_5$ the known quantities are as follows:

$a_1(t_5)$, $\theta_1(t_5)$, $d\theta_1/dt(t_5)$, $d^2\theta_1/dt^2(t_5)$, $a_2(t_5)$, $\theta_2(t_5)$, $d\theta_2/dt(t_5)$, $d^2\theta_2/dt^2(t_5)$, $a_3(t_5)$, $\theta_3(t_5)$.

These data are still insufficient to describe the motion of the structure.

At time $t_6$, the known quantities relating to the segments of ranks 1 to 5 are respectively as follows:

$a_1(t_6)$, $\theta_1(t_6)$, $d\theta_1/dt(t_6)$, $d^2\theta_1/dt^2(t_6)$, $a_2(t_6)$, $\theta_2(t_6)$, $d\theta_2/dt(t_6)$, $d^2\theta_2/dt^2(t_6)$, $a_3(t_6)$, $\theta_3(t_6)$, $d\theta_3/dt(t_6)$.

These data are still insufficient to describe the motion of the structure.

At time $t_7$, the known quantities relating to the segments of ranks 1 to 5 are respectively as follows:

$a_1(t_7)$, $\theta_1(t_7)$, $d\theta_1/dt(t_7)$, $d^2\theta_1/dt^2(t_7)$, $a_2(t_7)$, $\theta_2(t_7)$, $d\theta_2/dt(t_7)$, $d^2\theta_2/dt^2(t_7)$, $a_3(t_7)$, $\theta_3(t_7)$, $d\theta_3/dt(t_7)$, $d^2\theta_3/dt^2(t_7)$, $a_4(t_7)$, $\theta_4(t_7)$.

These data are still insufficient to describe the motion of the structure.

At time $t_8$, the known quantities are as follows:

$a_1(t_8)$, $\theta_1(t_8)$, $d\theta_1/dt(t_8)$, $d^2\theta_1/dt^2(t_8)$, $a_2(t_8)$, $\theta_2(t_8)$, $d\theta_2/dt(t_8)$, $d^2\theta_2/dt^2(t_8)$, $a_3(t_8)$, $\theta_3(t_8)$, $d\theta_3/dt(t_8)$, $d^2\theta_3/dt^2(t_8)$, $a_4(t_8)$, $\theta_4(t_8)$, $d\theta_4/dt(t_8)$.

At time $t_9$ the known quantities are as follows:

$a_1(t_9)$, $\theta_1(t_9)$, $d\theta_1/dt(t_9)$, $d^2\theta_1/dt^2(t_9)$, $a_2(t_9)$, $\theta_2(t_9)$, $d\theta_2/dt(t_9)$, $d^2\theta_2/dt^2(t_9)$, $a_3(t_9)$, $\theta_3(t_9)$, $d\theta_3/dt(t_9)$, $d^2\theta_3/dt^2(t_9)$, $a_4(t_9)$, $\theta_4(t_9)$, $d\theta_4/dt(t_9)$, $d^2\theta_4/dt^2(t_9)$, $a_5(t_9)$, $\theta_5(t_9)$.

These data now make it possible to completely describe the motion of the structure. If the representation is continued for the subsequent times $t_{10}$ and $t_{11}$, this gives:

at time $t_{10}$, the known quantities relating to the segments of rank 1 to 5 are respectively as follows:
$a_1(t_{10})$, $\theta_1(t_{10})$, $d\theta_1/dt(t_{10})$, $d^2\theta_1/dt^2(t_{10})$,
$a_2(t_{10})$, $\theta_2(t_{10})$, $d\theta_2/dt(t_{10})$, $d^2\theta_2/dt^2(t_{10})$,
$a_3(t_{10})$, $\theta_3(t_{10})$, $d\theta_3/dt(t_{10})$, $d^2\theta_3/dt^2(t_{10})$
$a_4(t_{10})$, $\theta_4(t_{10})$, $d\theta_4/dt(t_{10})$, $d^2\theta_4/dt^2(t_{10})$
$a_5(t_{10})$, $\theta_5(t_{10})$, $d\theta_5/dt(t_{10})$; and at time $t_{11}$, the known quantities relating to the segments of rank 1 to 5 are respectively as follows:
$a_1(t_{11})$, $\theta_1(t_{11})$, $d\theta_1/dt(t_{11})$, $d^2\theta_1/dt^2(t_{11})$
$a_2(t_{11})$, $\theta_2(t_{11})$, $d\theta_2/dt(t_{11})$, $d^2\theta_2/dt^2(t_{11})$,
$a_3(t_{11})$, $\theta_3(t_{11})$, $d\theta_3/dt(t_{11})$, $d^2\theta_3/dt^2(t_{11})$,
$a_4(t_{11})$, $\theta_4(t_{11})$, $d\theta_4/dt(t_{11})$, $d^2\theta_4/dt^2(t_{11})$,
$a_5(t_{11})$, $\theta_5(t_{11})$, $d\theta_5/dt(t_{11})$, $d^2\theta_5/dt^2(t_{11})$.

The articulated motion of the structure with five segments is completely defined as soon as the accelerations and orientations of the five segments (n=5) are known, that is to say as from time $t_9$ (k=9). Likewise it is found for example that, for a structure with three segments (n=3), the accelerations and orientations of the three segments are known as from time $t_5$ (k=5).

It is thus possible to establish, between the integer number n and the integer number k, a relationship that translates the fact that the motion capture device is functioning correctly, that is to say delivers all the acceleration and orientation information necessary for all the segments of the structure. This relationship is written:

$$k > 2n-2$$

FIG. 6B illustrates, in the general case, the results of calculations of acceleration and orientation data obtained, gradually, for various segments of a structure with articulated segments. The calculation of the acceleration and orientation data is described below for the first three segments.

The Case of the First Segment

In a first step, the measurements $a_1(t_k)$ and $M_1(t_k)$ are used, which correspond respectively to the acceleration measured (or calculated) on the segment 1 (by virtue of the first measuring means ML) and the measurements delivered by the second measuring means (MD1). Use is also made of the orientations $\theta_1(t_{k-1})$ and $\theta_1(t_{k-2})$ of the first segment given (or calculated) for the previous times ($t_{k-1}$ et $t_{k-2}$).

By virtue of these four items of information it is possible to calculate the orientation of the segment 1 at time $t_k$: $\theta_1(t_k)$.

In a second step, $a_1(t_k)$ the acceleration measured (or calculated) on the segment 1 (by virtue of the first measuring means ML) is used, as well as the orientations of the first segment $\theta_1(t_k)$ calculated at the previous step and $\theta_1(t_{k-1})$ and $\theta_1(t_{k-2})$ those given (or calculated) for the previous times ($t_{k-1}$ and $t_{k-2}$). With these quantities the acceleration $a_2(t_k)$ at the articulation p2 is calculated.

The Case of the Second Segment

In a first step, the acceleration $a_2(t_k)$ calculated at the previous step and the measurements $M_2(t_k)$ of the measuring means $MD_2$ of the second segment are used at time $t_k$. Use is also made of the orientations $\theta_2(t_{k-1})$ and $\theta_2(t_{k-2})$ of the second segment given (or calculated) for the previous times ($t_{k-1}$ and $t_{k-2}$).

By virtue of these four items of information it is possible to calculate the orientation of the segment 1 at time $t_k$: $\theta_1(t_k)$.

In a second step, $a_2(t_k)$ the acceleration calculated at the second step of the first segment is used, as well as the orientations of the second segment $\theta_2(t_k)$ calculated at the previous step and $\theta_2(t_{k-1})$ and $\theta_2(t_{k-2})$ given (or calculated) for the previous times ($t_{k-1}$ and $t_{k-2}$). With these quantities the acceleration $a_3(t_k)$ at the articulation p3 is calculated.

The Case of the Third Segment

The same two steps are carried out as for the second segment, substituting the index 4 for the index 3, the index 3 for the index 2 and the index 2 for the index 1.

This continues as far as the $N^{th}$ segment: the same two steps are performed as for the second segment, substituting the index N+1 for the index 3, the index N for the index 2 and the index N-1 for index 1.

When all the segments have been considered, the following time $t_k$ is awaited in order to recommence.

In the general case, it should be noted that, in order to know the estimated orientation of a segment at time $t_k$, it is necessary to know the estimated orientations of this same segment at the previous two times $t_{k-1}$ and $t_{k-2}$. Consequently, for the first calculation time, it is necessary to initialise the values of the orientations at the previous times. For this purpose it will be possible for example to make static measurements for which the accelerations are low and may consequently be ignored; the angles can then be calculated as described in patent application FR 2 838 185. It is also possible to use other means for initialising the angles (angular coders, set to a stressed initial position, etc).

Figure 7A:
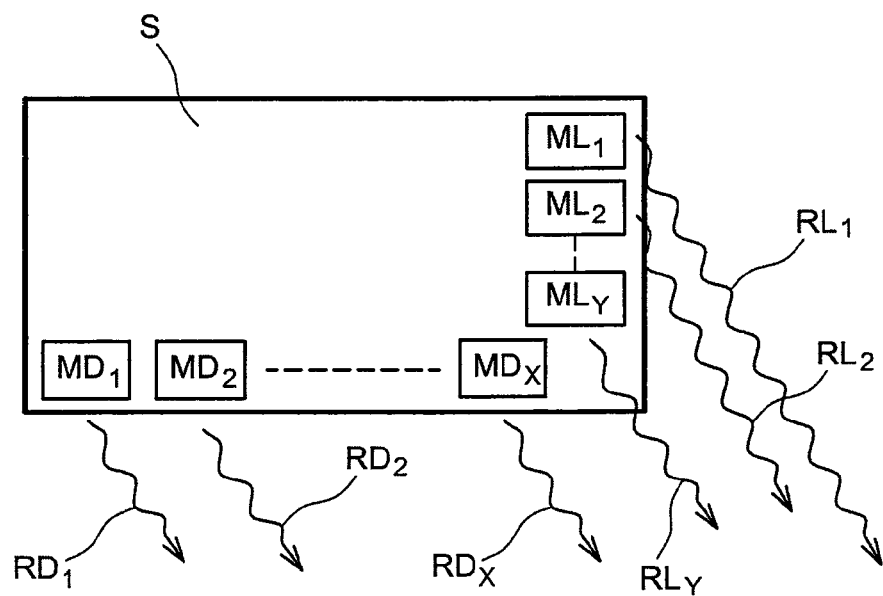
FIGS. 7A and 7B depict two embodiments of a motion reproduction device according to the invention.
Figure 7A:
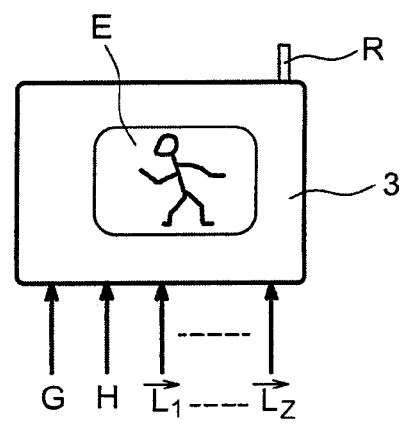
Figure 7B:
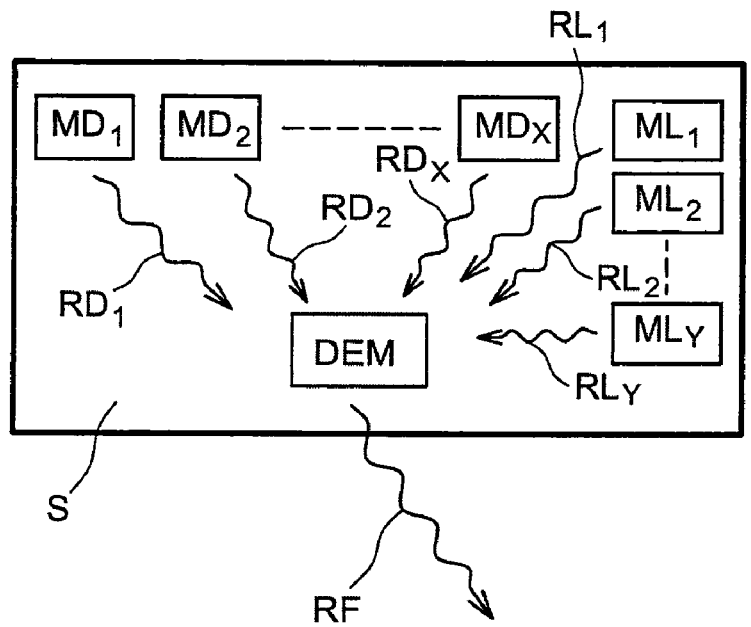
Figure 7B:
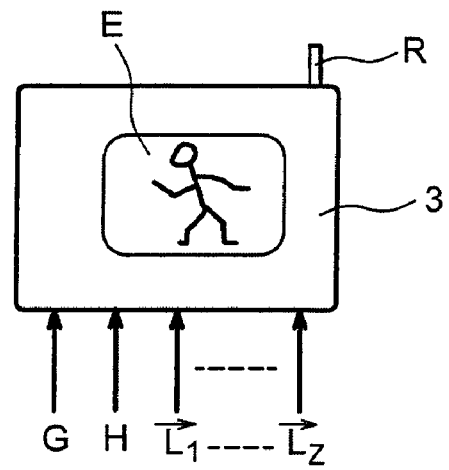

FIGS. 7A and 7B depict two embodiments of a motion reproduction device according to the invention. The structure S consisting of n articulated segments is represented symbolically by a rectangle. The structure S, for example a man or a robot, is provided with a set of devices $MD_i$ (i=1, 2, ..., n) and a set of local measurement systems $ML_j$ (j=1, 2, ..., m). The devices $MD_i$ and the systems $ML_j$ are distributed over the structure as described previously. As also described previously, although m local measurement systems are shown in FIGS. 7A and 7B, a single system of local measurements suffices to implement the invention.

In the first embodiment (FIG. 7A), the measurements delivered by the devices $MD_i$ and the measurements delivered by the local measurement systems $ML_j$ are transmitted, by the respective radio signals $RD_i$ and $RL_j$, to a calculation system 3, for example a computer. The motion reproduction device then comprises radio transmission means. The calculation system 3 is provided with a reception antenna R that receives the signals $RD_i$ and $RL_j$. The calculation system 3 also receives, as input parameters, the value G of the local gravitation field in the reference frame, the value H of the local magnetic field in the reference frame and the coordinates of the various vectors $\vec{L}_i$, (i=1, 2, ..., n) that represent the various segments.

The calculation system 3 then implements a data process in accordance with what was described above with reference to FIGS. 5 and 6. A display device E, for example a screen, then displays the motion of the articulated structure.

FIG. 7B differs from FIG. 7A in that the radio signals $RD_i$ and $RL_j$ are not here directly transmitted to the calculation system 3 but are transmitted to an intermediate unit DEM fixed to the structure S. The unit DEM then transmits the data that it receives in the form of a radio signal RF to the calculation system 3.

The presence of an intermediate unit DEM on the structure S advantageously makes it possible to implement another embodiment of the invention. This is because, in the case where the structure S moves at a great distance from the calculation system 3, it is possible that the range of the RF signal may deteriorate. A memory card placed in the intermediate unit DEM can then record the signals $RD_i$ and $RL_j$. The processing of the data can then be carried out subsequently to the capture of the measurements, once the movement is executed, from the reading of the data recorded on the memory card.

The invention claimed is:

1. Motion capture device of a structure consisting of N successive solid segments articulated with respect to one another from a segment of rank 1 as far as a segment of rank N, N being an integer number greater than or equal to 2, the segment of rank n (n=2, . . . , N) being articulated with the segment of rank n−1 at an articulation point $p_n$, the motion capture device comprising:

first means (ML) that deliver information able to restore an absolute acceleration vector $\vec{a}_1$ of a point on the segment of rank 1 in a reference frame forming a reference, at successive times $t_k$, k being an integer number greater than or equal to 1, second measuring means ($MD_1$) fixed to the segment of rank 1 and which deliver, at each time $t_k$, a measurement ($M_1$) representing an orientation vector $\vec{\Theta}_1$ of the segment of rank 1 in the reference frame, and supplementary measurement means ($MD_n$) fixed to each segment of rank n (n=2, . . . , N), and which deliver, at each time $t_k$, a measurement representing an orientation vector $\vec{\Theta}_n$ of the segment of rank n.

2. Motion capture device according to claim 1, in which the second measuring means ($MD_1$) and the supplementary measuring means ($MD_n$) consist of an accelerometer and a sensor that delivers a measurement of a uniform physical field present in the space where the structure moves and with a known direction in the reference frame.

3. Motion capture device according to claim 2, in which the second measuring means ($MD_1$) and the supplementary measuring means ($MD_n$) further comprise at least one gyrometric axis.

4. Motion capture device according to claim 2, in which the sensor that delivers a measurement of a uniform physical field of known direction in the reference frame is a magnetometer.

5. Motion capture device according to claim 2, in which the sensor that delivers a measurement of a uniform physical field of known direction in the reference frame is a photoelectric cell.

6. Device according to claim 1, in which the first means (ML) are measuring means consisting of a velocity measurer so that the data item able to restore an absolute acceleration vector of the segment of rank 1 is the velocity of the point.

7. Device according to claim 1, in which the first means (ML) are measuring means consisting of a position measurer so that the data item able to restore an absolute acceleration vector of a point on the segment of rank 1 is the position of the point.

8. Device for reproducing the motion of a structure consisting of N successive solid segments articulated with respect to one another from a segment of rank 1 as far as a segment of rank N, N being an integer number greater or equal to 2, the segment of rank n (n=2, . . . , N) being articulated with the segment of rang n−1 at an articulation point $p_n$, the device comprising:

a motion capture device according to claim 1 in which the supplementary measurement means ($MD_n$) of a segment of rank n are positioned close to the articulation point $p_n$ so that the distance that separates the supplementary measuring means ($MD_n$) of a segment of rank n from the articulation point $p_n$ is considered to be zero, and calculation means (3) that calculate, at each time $t_k$:

a) the absolute acceleration vector $\vec{a}_1$ in the reference frame, from the information delivered by the first means, b) the orientation vector $\vec{\Theta}_1$ of the segment of rank 1 in the reference frame, from the absolute acceleration vector $\vec{a}_1$ and the measurement ($M_1$) representing the orientation vector ($\vec{\Theta}_1$) of the segment of rank 1;

c) an acceleration vector $\vec{a}_n$ (n>2) of the articulation point $p_n$ in the reference frame, from the equation:

$$\vec{a}_n = \vec{a}_{n-1} + \left(\frac{d\vec{\omega}_{n-1}}{dt}\right) \wedge \overrightarrow{L_{n-1}} + \vec{\omega}_{n-1} \wedge (\vec{\omega}_{n-1} \wedge \overrightarrow{L_{n-1}})$$

where $\vec{\omega}_n = d(\vec{\Theta}_n)/dt$, $\vec{L}_n$ being a vector oriented from the articulation point $p_{n-1}$ to the articulation point $p_n$ and whose modulus has as its value the distance that separates the articulation point $p_n$ from the articulation point $p_{n-1}$; and d) the orientation vector $\vec{\Theta}_n$ (n>2) of the segment of rank n from the acceleration vector $\vec{a}_n$ and the measurement ($M_n$) representing the orientation of the segment of rank n.

9. Device for reproducing the motion of a structure consisting of N successive solid segments articulated with respect to one another from a segment of rank 1 as far as a segment of rank N, N being an integer number greater than or equal to 2, the segment of rank n (n=2, . . . , N) being articulated with the segment of rank n−1 at an articulation point $p_n$, the device comprising:

a motion capture device according to claim 1 in which the supplementary measuring means ($MD_n$) of a segment of rank n are distant from the articulation point $p_n$, and calculation means (3) that calculate, at each time $t_k$:

a) the absolute acceleration vector $\vec{a}_1$ in the reference frame, from the information delivered by the first means, b) the orientation vector $\vec{\Theta}_1$ of the segment of rank 1 in the reference frame, from the absolute acceleration vector $\vec{a}_1$ and the measurement ($M_1$) representing the orientation vector $\vec{\Theta}_1$ of the segment of rank 1;

c) an acceleration vector $\vec{a}_n$ (n>2) of the articulation point $p_n$ in the reference frame, from the equation:

$$\vec{a}_n = \vec{a}_{n-1} + \left(\frac{d\vec{\omega}_{n-1}}{dt}\right) \wedge \overrightarrow{L_{n-1}} + \vec{\omega}_{n-1} \wedge (\vec{\omega}_{n-1} \wedge \overrightarrow{L_{n-1}})$$

where $\vec{\omega}_n = d(\vec{\Theta}_n)/dt$, $\vec{L}_n$ being a vector oriented from the articulation point $p_{n-1}$ to the articulation point $p_n$ and whose modulus has as its value the distance that separates the articulation point $p_n$ from the articulation point $p_{n-1}$; and d) the orientation vector $\vec{\Theta}_n$ (n>2) and an acceleration vector $\vec{b}_n$ of the measuring point of the supplementary measuring means fixed on the segment of rank n from the acceleration vector $\vec{a}_n$, the measurement ($M_n$) representing the orientation of the segment of rank n, and the orientation vectors of the segment of rank n at least two times that precede the time $t_k$, with $\vec{b}_n$ such that:

$$\vec{b}_n = \vec{a}_n + \left(\frac{d\vec{\omega}_n}{dt}\right) \wedge \vec{D}_n + \vec{\omega}_n \wedge (\vec{\omega}_n \wedge \vec{D}_n)$$

where $\vec{D}_n$ is a vector oriented from the articulation point $p_n$ to the supplementary measuring means of the segment of rank n and whose modulus is substantially equal to the distance that separates the articulation point $p_n$ from the supplementary measuring means of the segment of rank n.

10. Motion reproduction device according to claim 8, in which radio transmission means transmit elementary electrical signals ($RD_n$, $RL_m$) representing the measurements delivered by the first measuring means (ML) and the second measuring means ($MD_n$) to the calculation means (3).

11. Motion reproduction device according to claim 10, in which the transmission means comprise an intermediate unit (DEM) that receives the elementary electrical signals ($RD_1$, . . . , $RD_X$, $RL_1$, . . . , $RL_Y$) and that retransmits an electrical signal (RF) representing elementary electrical signals to the calculation means (3).

12. Motion reproduction device according to claim 9, in which radio transmission means transmit elementary electrical signals ($RD_n$, $RL_m$) representing the measurements delivered by the first measuring means (ML) and the second measuring means ($MD_n$) to the calculation means (3).

13. Motion reproduction device according to claim 12, in which the transmission means comprise an intermediate unit (DEM) that receives the elementary electrical signals ($RD_1$, . . . , $RD_X$, $RL_1$, . . . , $RL_Y$) and that retransmits an electrical signal (RF) representing elementary electrical signals to the calculation means (3).

14. Device according to claim 1, in which storage means store the measurements delivered by the first measuring means (ML) and the second measuring means ($MD_n$).

15. Device according to claim 14, in which the storage means are placed on the structure.

16. Method of capturing the motion of a structure consisting of N successive solid segments articulated with respect to one another from a segment of rank 1 as far as a segment of rank N, N being an integer number greater than or equal to 2, the segment of rang n (n=2, . . . , N) being articulated with the segment of rank n−1 at an articulation point $p_n$, the method comprising:
    obtaining from a first device at least one determination of an item of information able to restore an absolute acceleration vector $\vec{a}_1$ of a point on the segment of rank 1 in a reference frame, at successive times $t_k$, k being an integer number greater than or equal to 1,
    obtaining from a second device at least one measurement representing an orientation vector $\vec{\Theta}_1$ of the segment of rank 1 in the reference frame, at each of the successive times $t_k$, and
    obtaining from a supplementary device for each segment of rank n, at least one supplementary measurement of an orientation vector $\vec{\Theta}_n$ of the segment of rank n in the reference frame, at each of the successive times $t_k$.

17. Motion capture method according to claim 16, in which the measurement representing the orientation vector $\vec{\Theta}_1$ of the segment of rank 1 in the reference frame and the measurement representing the orientation vector $\vec{\Theta}_n$ of the segment of rank n are each a measurement of a uniform field present in the space where the structure moves and with a known direction in the reference frame.

18. Motion capture method according to claim 16, in which the information able to restore an absolute acceleration vector $\vec{a}_1$ of a point on the segment of rank 1 in a reference frame is the velocity of the point in the reference frame.

19. Motion capture method according to claim 16, in which the information able to restore an absolute acceleration vector $\vec{a}_1$ of a point on the segment of rank 1 in a reference frame is the position of the point in the reference frame.

20. Method for reproducing the motion of a structure consisting of N successive solid segments articulated with respect to one another from a segment of rank 1 as far as a segment of rank N, N being an integer number greater than or equal to 2, the segment of rang n (n=2, . . . , N) being articulated with the segment of rank n−1 at an articulation point $p_n$, the method comprising:
    performing the motion capture method according to claim 16, and
    performing a calculation by a calculation system, at each time $t_k$:
    a) of the absolute acceleration vector $\vec{a}_1$ in the reference frame, from the measurement able to restore an absolute acceleration vector $\vec{a}_1$,
    b) of the orientation vector $\vec{\Theta}_1$ of the segment of rank 1 in the reference frame, from the absolute acceleration vector $\vec{a}_1$ and the measurement ($M_1$) representing the orientation vector ($\vec{\Theta}_1$) of the segment of rank 1;
    c) of an acceleration vector $\vec{\Theta}_n$ (n≥2) of the articulation point $p_n$ in the reference frame, from the equation:

$$\vec{a}_n = \vec{a}_{n-1} + \left(\frac{d\vec{\omega}_{n-1}}{dt}\right) \wedge \overrightarrow{L_{n-1}} + \vec{\omega}_{n-1} \wedge (\vec{\omega}_{n-1} \wedge \overrightarrow{L_{n-1}})$$

where $\vec{\omega}_n = d(\vec{\Theta}_n)/dt$, $\vec{L}_n$ being a vector oriented from the articulation point $p_{n-1}$ towards the articulation point $p_n$ and whose modulus has as its value the distance that separates the articulation point $p_n$ from the articulation point $p_{n-1}$, the supplementary measurement representing the orientation vector $\vec{\Theta}_n$ being delivered by fixed measuring means, on the segment of rank n, substantially at the articulation point $p_n$; and
    d) of an orientation vector $\vec{\Theta}_n$ (n≥2) of the segment of rank n from the acceleration vector $\vec{a}_n$ and the measurement ($M_n$) representing the orientation of the segment of rank n.

21. Method for reproducing motion of a structure consisting of N successive solid segments articulated with respect to one another from a segment of rank 1 as far as a segment of rank N, N being an integer number greater or equal to 2, segment of rank n (n=2, . . . , N) being articulated with the segment of rang n−1 at an articulation point $p_n$, the method comprising:
    performing the motion capture method according to claim 16; and
    performing a calculation by a calculation system, at each time $t_k$:
    a) of the absolute acceleration vector $\vec{a}_1$ in the reference frame, from the information delivered by the first means,
    b) of the orientation vector $\vec{\Theta}_1$ of the segment of rank 1 in the reference frame, from the absolute acceleration vector $\vec{a}_1$ and the measurement ($M_1$) representing the orientation vector $\vec{\Theta}_1$ of the segment of rank 1;

c) of an acceleration vector $\vec{a}_n$ ($n \geq 2$) of the articulation $p_n$ in the reference frame, from the equation:

$$\vec{a}_n = \vec{a}_{n-1} + \left(\frac{d\vec{\omega}_{n-1}}{dt}\right) \wedge \vec{L}_{n-1} + \vec{\omega}_{n-1} \wedge (\vec{\omega}_{n-1} \wedge \vec{L}_{n-1})$$

where $\vec{\omega}_n = d(\vec{\Theta}_n)/dt$, $\vec{L}_n$ being a vector oriented from the articulation point $p_{n-1}$ to the articulation point $p_n$ and whose modulus has as its value the distance that separates the articulation point $p_n$ from the articulation point $p_{n-1}$; and d) the orientation vector $\vec{\Theta}_n$ ($n \geq 2$) and an acceleration vector $\vec{b}_n$ of the measuring point of the supplementary measuring means fixed on the segment of rank n from the acceleration vector $\vec{a}_n$, the measurement ($M_n$) representing the orientation of the segment of rank n, and orientation vectors of the segment of rank n at least two times that precede the time $t_k$, with $\vec{b}_n$ such that:

$$\vec{b}_n = \vec{a}_n + \left(\frac{d\vec{\omega}_n}{dt}\right) \wedge \vec{D}_n + \vec{\omega}_n \wedge (\vec{\omega}_n \wedge \vec{D}_n)$$

where $\vec{D}_n$ is a vector oriented from the articulation point $p_n$ to the supplementary measuring means of the segment of rank n and whose modulus is substantially equal to the distance that separates the articulation point $p_n$ from the supplementary measuring means of the segment of rank n.

* * * * *

UNITED STATES PATENT AND TRADEMARK OFFICE
CERTIFICATE OF CORRECTION

| | |
|---|---|
| PATENT NO. | : 8,055,021 B2 |
| APPLICATION NO. | : 12/279619 |
| DATED | : November 8, 2011 |
| INVENTOR(S) | : Yanis Caritu et al. |

Page 1 of 1

It is certified that error appears in the above-identified patent and that said Letters Patent is hereby corrected as shown below:

In Column 10, line 4 please delete " $= F\{K(\vec{a}_n(t_k), \vec{\Theta}_n(t_{j<k}), \vec{\Theta}_n(t_k)), G, H, \vec{\Theta}_n(t_k)]$ " and insert -- $= F[K(\vec{a}_n(t_k), \vec{\Theta}_n(t_{j<k}), \vec{\Theta}_n(t_k)), G, H, \vec{\Theta}_n(t_k)]$ -- therefore.

In Column 18, line 30 please delete " $\vec{\Theta}_n \ (n \geq 2)$ " and insert -- $\vec{a}_n \ (n \geq 2)$ -- therefore.

Signed and Sealed this

Twenty-sixth Day of June, 2012

David J. Kappos
*Director of the United States Patent and Trademark Office*